(12) United States Patent
Swanson et al.

(10) Patent No.: US 8,838,255 B2
(45) Date of Patent: Sep. 16, 2014

(54) ASSEMBLY KIT FOR CREATING PADDLE-STYLE LEAD FROM ONE OR SEVERAL PERCUTANEOUS LEADS AND METHOD OF LEAD IMPLANTATION

(75) Inventors: John W. Swanson, Portland, OR (US); Christopher S. L. Crawford, Frisco, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 432 days.

(21) Appl. No.: 13/230,210

(22) Filed: Sep. 12, 2011

(65) Prior Publication Data

US 2011/0319973 A1    Dec. 29, 2011

Related U.S. Application Data

(62) Division of application No. 11/877,282, filed on Oct. 23, 2007, now Pat. No. 8,019,442.

(60) Provisional application No. 60/862,909, filed on Oct. 25, 2006.

(51) Int. Cl.
*A61N 1/05*    (2006.01)

(52) U.S. Cl.
CPC ..................................... *A61N 1/0551* (2013.01)
USPC .......................................................... 607/117

(58) Field of Classification Search
USPC .......................................... 607/115–120, 148
See application file for complete search history.

(56) References Cited

U.S. PATENT DOCUMENTS

| | | | |
|---|---|---|---|
| 5,405,372 A * | 4/1995 | Gilljam et al. ................. | 607/115 |
| 6,658,302 B1 | 12/2003 | Kuzma et al. | |
| 2005/0004639 A1 | 1/2005 | Erickson | |
| 2005/0033393 A1 | 2/2005 | Daglow | |
| 2005/0137668 A1 | 6/2005 | Khan | |
| 2005/0171587 A1 | 8/2005 | Daglow et al. | |
| 2005/0288759 A1 | 12/2005 | Jones et al. | |

* cited by examiner

*Primary Examiner* — Luther Behringer

(57) ABSTRACT

In one embodiment, an assembly for conducting pulses from an implantable pulse generator, comprises: at least one percutaneous lead comprising terminals and at least two groups of electrodes, each group of electrodes possessing an intra-group electrode spacing; a frame member comprising first and second arms, the frame member comprising an inner lumen for removably housing the at least one percutaneous lead, each arm of the first and second arms comprising a plurality of apertures that are spaced according to the intra-group electrode spacing to allow conduction of electrical pulses from the electrodes of the at least one percutaneous lead to tissue of the patient when the lead is positioned within the frame member; and a spring member that is connected to the frame member for maintaining the first and second arms of the frame member at a predetermined distance in the absence of an external force on the spring member.

10 Claims, 3 Drawing Sheets

ASSEMBLY KIT FOR CREATING PADDLE-STYLE LEAD FROM ONE OR SEVERAL PERCUTANEOUS LEADS AND METHOD OF LEAD IMPLANTATION

RELATED APPLICATIONS

This application is a divisional of U.S. application Ser. No. 11/877,282, filed Oct. 23, 2007, now U.S. Pat. No. 8,019,442, which claims the benefit of U.S. Provisional Application No. 60/862,909, filed Oct. 25, 2006, the disclosure of which is incorporated herein by reference.

BACKGROUND

The present application is generally related to an assembly kit for creating paddle-style lead using one or several percutaneous leads and method of lead implantation.

Application of electrical fields to spinal nerve roots, spinal cord, and other nerve bundles for the purpose of chronic pain control has been actively practiced for some time. While a precise understanding of the interaction between the applied electrical energy and the nervous tissue is not fully appreciated, it is known that application of an electrical field to spinal nervous tissue (i.e., spinal nerve roots and spinal cord bundles) can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

It is known that each exterior region, or each dermatome, of the human body is associated with a particular longitudinal spinal position. Thus, electrical stimulation of spinal nerve tissue must occur at a specific longitudinal location to effectively treat chronic pain. Additionally, it is important to avoid applying electrical stimulation of nerve tissue associated with regions of the body that are unaffected by chronic pain. Positioning of an applied electrical field relative to a physiological midline is also important.

Percutaneous leads and laminotomy leads are the two most common types of lead designs that provide conductors that deliver stimulation pulses from an implantable pulse generator (IPG) to distal electrodes adjacent to the nerve tissue. As shown in FIG. 1A, conventional percutaneous lead 100 includes electrodes 101 that substantially conform to the body of the body portion of the lead. Due to the relatively small profile of percutaneous leads, percutaneous leads are typically positioned above the dura layer through the use of a Touhy-like needle. Specifically, the Touhy-like needle is passed through the skin, between desired vertebrae to open above the dura layer for the insertion of the percutaneous lead.

As shown in FIG. 1B, conventional laminotomy or paddle lead 150 has a paddle configuration and typically possesses a plurality of electrodes 151 arranged in multiple columns. Multi-column laminotomy leads enable reliable positioning of a plurality of electrodes. Also, laminotomy leads offer a more stable platform that tends to migrate less after implantation and that is capable of being sutured in place. Laminotomy leads also create a unidirectional electrical field and, hence, can be used in a more electrically efficient manner than conventional percutaneous leads. Due to their dimensions and physical characteristics, conventional laminotomy leads require a surgical procedure for implantation. The surgical procedure (a partial laminectomy) is invasive and requires the resection and removal of certain vertebral bone tissue to allow both access to the dura and proper positioning of a laminotomy lead.

BRIEF SUMMARY

Some representative embodiments are directed to an assembly kit for receiving one or several percutaneous leads. The assembly kit includes a frame member through which the percutaneous leads are threaded. The frame member comprises first and second arms for receiving the percutaneous leads. In each arm, the frame member comprises apertures that correspond to the positions and spacing of the electrodes of the percutaneous leads. During assembly, the percutaneous leads are advanced through the frame member until the electrodes are exposed through the apertures. A spring member is attached to the frame member to provide a mechanical bias to retain the arms with their leads at a desired width when an external compressive force is not applied to the spring member. Also, a thin film member is preferably disposed between the first and second arms to prevent tissue in-growth between the two percutaneous leads after implantation.

During the implantation process, a suitable hollow-channel insertion tool is inserted within the epidural space of the patient according to one representative embodiment. The distal end with the spring member is inserted into the suitable hollow-channel insertion tool. The shape of the spring member allows the spring member and the arms of the frame member to be inwardly compressed to assume a relatively small profile. The compression of the spring member and the frame member enables the implantation to occur through a relatively small insertion tool thereby reducing the trauma to the patient. The spring member, the frame member, and the lead(s) are advanced into the epidural space through the insertion tool. Accordingly, removal of bone tissue is not required. Upon exiting the insertion tool, the spring member causes the arms of the frame member to be separated by the desired amount of space and thereby cause the electrodes of the stimulation lead(s) to be positioned in a manner similar to a paddle lead. The stimulation leads can then be utilized for spinal cord stimulation and the relative positions of the electrodes will remain fixed. Also, the field applied by the electrodes will be substantially unidirectional.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

Figure 1A:
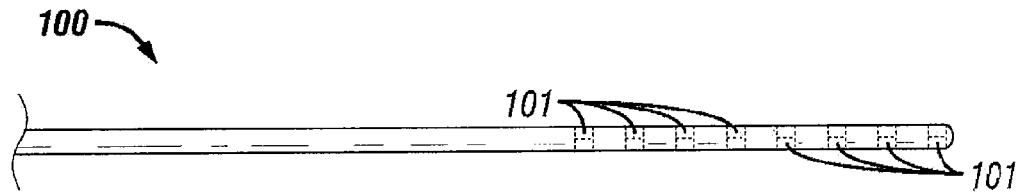
FIGS. 1A and 1B depict conventional percutaneous and paddle leads respectively.
Figure 1B:
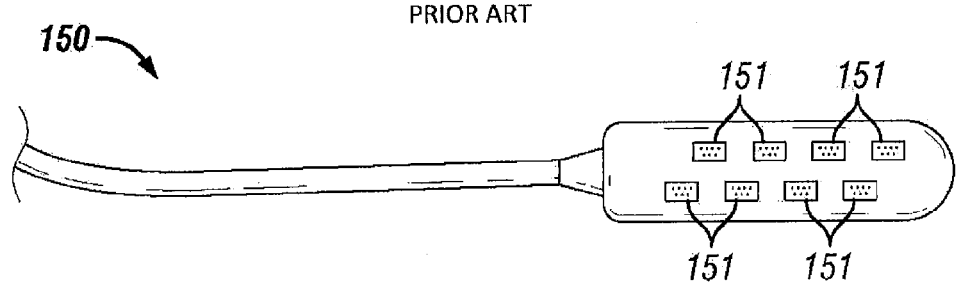
Figure 2A:
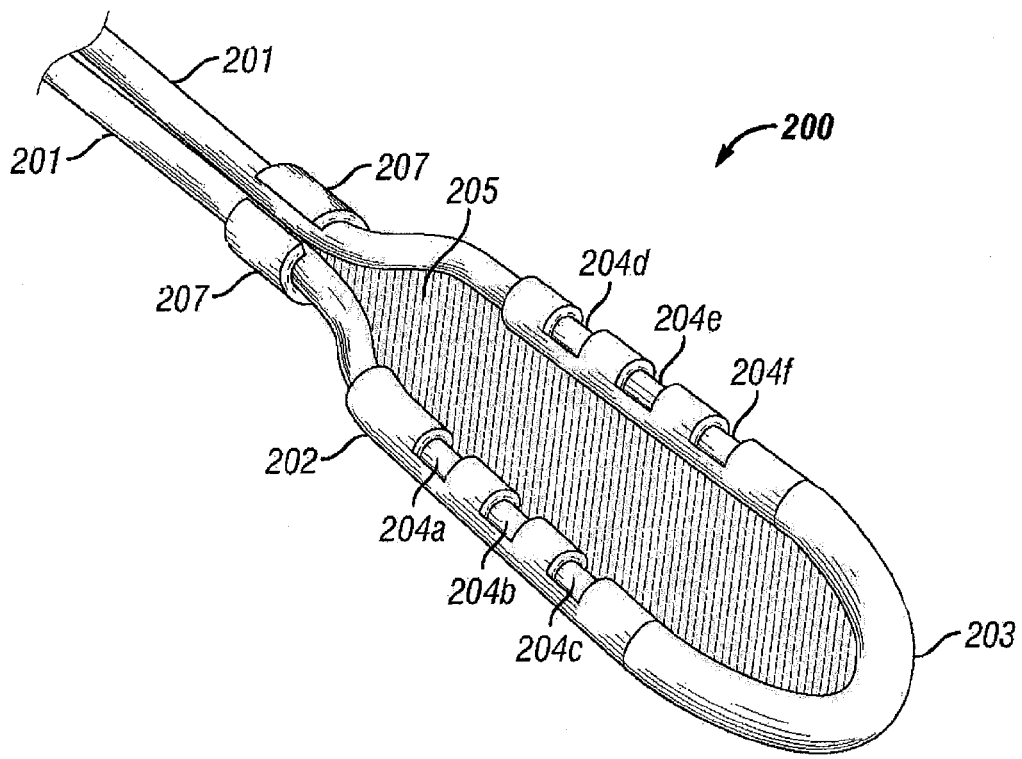
FIG. 2A depicts a paddle-style assembly kit for percutaneous leads according to one representative embodiment.

Referring now to FIG. 2A, assembly kit 200 is shown according to one representative embodiment. Assembly kit 200 comprises frame member 202 that comprises parallel arms. Frame member 202 is preferably fabricated from a relatively high durometer, biocompatible, biostable polymer. Examples of suitable polymers include polyetheretherketone (PEEK) and polyether-ketone ketone (PEKK). Frame member 202 comprises a set of apertures 204 on each arm of frame member 202 (which are shown collectively as 204a-204f). Apertures 204 can be formed by ablating through the polymer material using a suitable laser. Although only six apertures are shown in FIG. 2A for the sake of clarity, any number of apertures can be provided in frame member 202 to accommodate suitable percutaneous leads 201. Apertures 204 cause the field from electrodes positioned underneath apertures 204 to be substantially unidirectional. The unidirectional characteristic is advantageous, because it reduces the probability of undesired stimulation in spinal cord stimulation applications. Also, the unidirectional characteristic enables stimulation to occur at a reduced power consumption.

Assembly kit 200 further comprises spring member 203 that is attached to frame member 202. Spring member 203 may be permanently attached to frame member 202 during fabrication of these components or may be fabricated as a separate component for attachment by a surgeon. When assembled as shown in FIG. 2A, frame member 202 and spring member 203 can be collapsed to assume a relatively small profile to enable kit 200 to be inserted through a suitable implantation tool. An example of a surgical tool that can be utilized to implant kit 200 is described in U.S. Patent Application Publication No. 20050288759, entitled "Method and apparatus for implanting an electrical stimulation lead using a flexible introducer," which is incorporated herein by reference. When kit 200 exits the introducer instrument into the epidural space, spring member 203 is no longer subjected to a compressive force and expands the arms of frame member 202 to the predetermined distance. Hence, electrodes of lead (s) 201 are then positioned within the epidural space in a manner that is similar to an electrode spacing provided by a paddle-style lead.

One advantage of allowing the surgeon to attach spring member 203 during the implantation procedure is that multiple sets of spring members 203 could be provided with each set having different spring characteristics. The surgeon could select a spring member 203 having a greater spring constant if assembly kit 200 does not sufficiently expand in the epidural space using another spring member 203 due to fibrosis or other tissue obstructions. Additionally, to prevent fibrosis or other tissue in-growth from occurring after implantation, thin membrane 205 is provided between the arms of frame member 202. Thin membrane 205 can be fabricated from a low durometer, elastic Carbosil material as an example. By utilizing membrane 205, kit 200 can be more readily explanted if subsequently necessary.

Figure 2B:
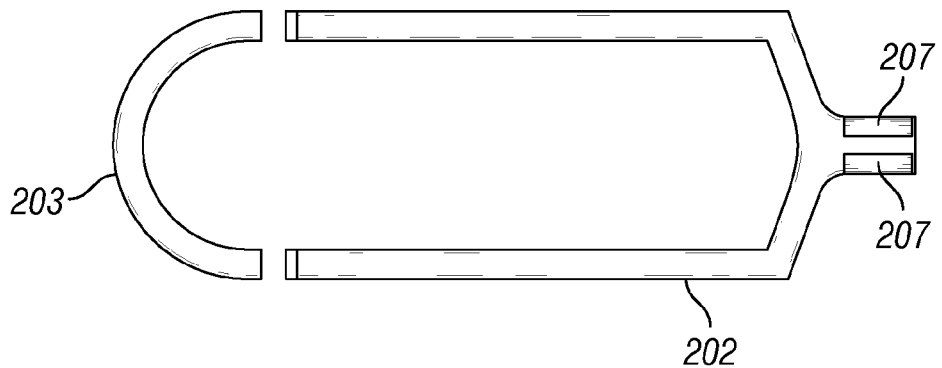
FIG. 2B depicts a disassembled view of a frame member and spring member according to one representative embodiment.

Spring member 203 is also preferably fabricated from PEEK material which possesses a spring memory characteristic. Other suitable biocompatible, biostable polymers can be employed such as PEKK. If spring member 203 is fabricated as a separate component from frame member 202 as shown in FIG. 2B, complementary connector structures (not shown) are provided on frame member 202 and spring member 203 to facilitate their coupling. In some alternative embodiments, metal spring elements are provided within spring member 203 to provide or augment the spring characteristic of spring member 203. However, metal spring elements can cause undesired tissue heating during an MRI procedure due to current induction from the strong time-varying RF fields generated by the MRI system. Accordingly, an all plastic structure is preferred to avoid current induction during an MRI procedure.

Spring member 203 is also preferably shaped so that when the end of spring member 203 encounters the inner wall of an insertion tool, the contact force tends to "pinch" spring member 203 thereby providing a compressive force to spring member 203. In response to the compressive force, spring member 203 collapses the arms of frame member 202 thereby allowing kit 200 to assume a profile that allows kit 200 to be advanced through the insertion tool.

Any suitable percutaneous lead(s) 201 can be employed within kit 200 provided that the electrode spacing of the lead(s) 201 corresponds to the spacing of apertures in frame 202. In one embodiment, a respective percutaneous lead is inserted within each arm of frame member 202. An example of a suitable commercially available lead for assembly kit 200 is the Axxess® lead available from Advanced Neuromodulation Systems, Inc. (Plano, Tex.). To retain each percutaneous lead 201 within frame, retention clips 207 are provided. Additionally, retention clips 207 facilitate the removal of frame member 202 from the epidural space when leads 201 are explanted.

Figure 3:
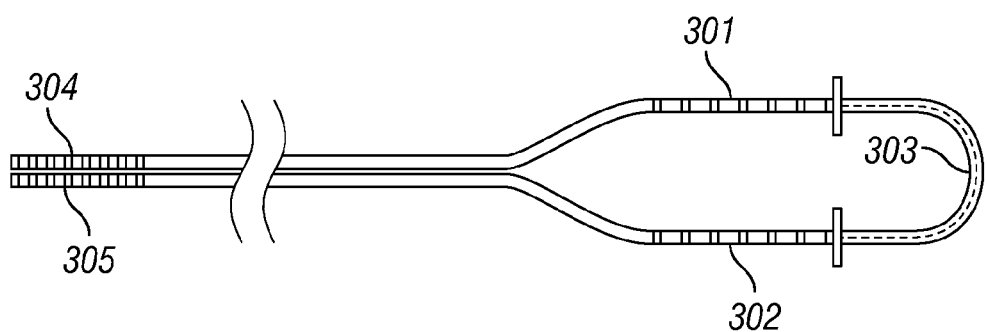
FIG. 3 depicts a percutaneous lead adapted according to one representative embodiment.

In one embodiment as shown in FIG. 3, a single lead is adapted to be threaded through both arms of frame member 202 of an assembly kit. Specifically, first and second groups 301 and 302 of electrodes are disposed on the single lead. Electrode groups 301 and 302 are disposed somewhat in the "middle" of the body of the lead. The intra-group electrode spacing in the lead corresponds to the spacing between adjacent apertures 204 in frame member 202. Also, the two groups of electrodes are separated on the body of the lead by distance 303 that corresponds to the distance between the two most distal apertures (204c and 204f in the specific embodiment of FIG. 2) including the distance along spring member 203. The lead as shown in FIG. 3 also comprises respective groups of terminals 304 and 305 at the proximal and distal ends of the lead. Each terminal of the groups 304 and 305 is electrically coupled to a respective electrode of groups 301 and 302 by a respective conductive wire embedded within the insulative body of the lead. The positioning of the groups 301, 302, 304, and 305 of electrodes and terminals enables lead 201 to be looped through kit 200. The looping of the lead through kit 200 is advantageous for explantation of frame member 202 and spring member 203.

Figure 4:
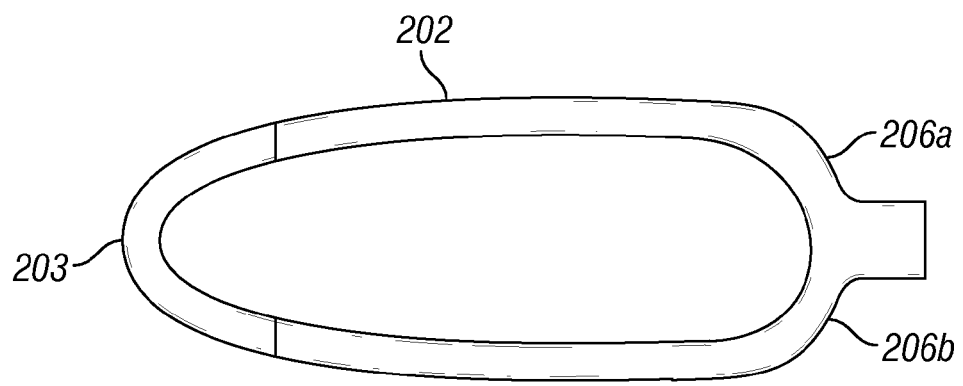
FIG. 4 depicts a "rear" view of a frame member and spring member according to one representative embodiment.

Also, to facilitate explantation, the proximal portion of frame member 202 is shaped at locations 206a and 206b to contact the inner wall of the insertion tool as shown in FIG. 4. In an explantation procedure, frame 202, spring member 203, and lead 201 are removed from the epidural space of a patient through the same type of surgical tool used for the implantation procedure. Essentially, the surgeon places the tool over the proximal ends of the lead and advances the tool until the epidural space of the patient is accessed. In a preferred embodiment, a strengthening wire member is inserted within an inner lumen of the lead to facilitate the explantation.

After insertion of the strengthening wire member and positioning of the open channel tool, the surgeon "pulls" on the lead and the strengthening wire member. The pulling force causes the lead, frame member 202, and spring member 203 to move up to the distal end of the tool. When the proximal end of frame member 202 contacts the inner wall of the tool, the resulting force pushes against locations 206a and 206b and the force is transferred from the arms of frame member 202 to spring member 203. The transferred force tends to elongate the frame and spring member 203 thereby compressing spring member 203 and bringing the arms of frame 202 together. Accordingly, the profile of frame 202 is reduced thereby allowing the kit 200 to be received within the open channel of the tool for removal from the epidural space.

In such a procedure, the benefit of looping the lead within the kit 200 is realized. Specifically, the looping of the lead enables the strengthening wire member to follow the entire perimeter of frame member 202 and spring member 203. Accordingly, a sufficient amount of force can be readily applied to ensure that spring member 203 is compressed to allow the withdrawal of the kit 200 through the surgical tool. Additionally, it shall be appreciated that explantation procedures according to representative embodiments involve relatively little complexity and do not require overly delicate manipulations.

Figure 5:
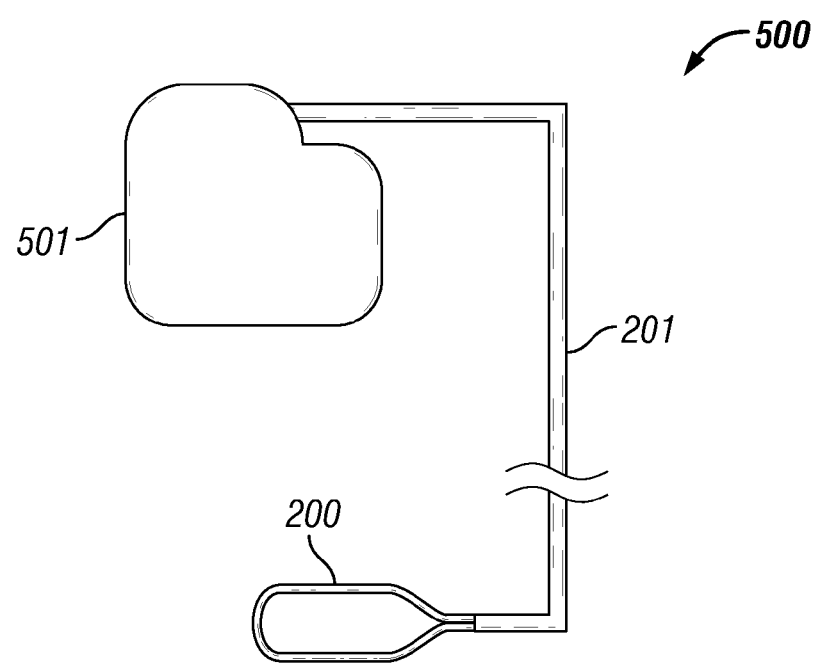
FIG. 5 depicts a stimulation system according to one representative embodiment.

FIG. 5 depicts stimulation system 500 according to one representative embodiment. System 500 comprises implantable pulse generator 501. An example of a commercially available pulse generator that can be used according to some representative embodiments is the Eon® stimulator available from Advanced Neuromodulation Systems, Inc. Pulse generator 501 is electrically coupled to lead 201 which is threaded through assembly kit 200. Lead 201 can be implanted in a patient without performing a laminectomy using a suitable implantation tool. After implantation in the epidural space of a patient, the positioning of the electrodes as provided by kit 201 allows lead 201 to function in a manner similar to paddle-style leads.

Although representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure that processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed:

1. An assembly kit for placing a stimulation lead for conducting electrical pulses from an implantable pulse generator to tissue in a patient, the assembly kit comprising:
   a stiffening stylet;
   at least one percutaneous lead comprising terminals and at least two groups of electrodes, each group of electrodes possessing an intra-group electrode spacing, wherein the at least one percutaneous lead comprises an internal lumen for receiving the stiffening stylet;
   a frame member comprising first and second arms, the frame member comprising an inner lumen for removably housing the at least one percutaneous lead, each arm of the first and second arms comprising a plurality of apertures that are spaced according to the intra-group electrode spacing to allow conduction of electrical pulses from the electrodes of the at least one percutaneous lead to tissue of the patient when the lead is positioned within the frame member;
   a spring member that is connected to the frame member for maintaining the first and second arms of the frame member at a predetermined distance in the absence of an external force on the spring member; and
   a tubular introducer for engaging the frame member during an implant or explant procedure;
   wherein (i) the frame member comprises a proximal end that is adapted to engage the tubular introducer, (ii) the internal lumen of the percutaneous lead is adapted to permit the stiffening stylet to extend along an entire length of the frame member to form a single loop extending through the tubular introducer and the first and second arms of the frame member, and (iii) application of a pulling force on the stylet when disposed in the single loop causes the proximal end of the frame member to contact the tubular introducer to collapse the frame member into the tubular introducer.

2. The assembly kit of claim 1 wherein the spring member exhibits a spring characteristic from polyetheretherketone (PEEK) material.

3. The assembly kit of claim 1 wherein the spring member comprises a metal element that provides a shape memory characteristic.

4. The assembly kit of claim 1 wherein the frame member is fabricated from polyetheretherketone (PEEK) material.

5. The assembly kit of claim 1 further comprising a thin membrane structure disposed between the first and second arms of the frame member.

6. The assembly kit of claim 1 wherein the spring member is attached to a distal end of the frame member.

7. The assembly kit of claim 6 wherein the spring member is removable from the frame member.

8. The assembly kit of claim 6 wherein the spring and frame members are fabricated from polyether-ketone ketone (PEKK).

9. The assembly kit of claim 1 wherein the at least one percutaneous lead is a single percutaneous lead, wherein the first and second groups of electrodes are spaced apart on a body of the single percutaneous lead by a distance equal to a distance between most distal apertures of the frame member including a distance along the spring member.

10. The assembly kit of claim 1 wherein the frame member further comprises one or several retention clips for retaining the at least one percutaneous lead.

* * * * *